United States Patent
Milton

(10) Patent No.: US 6,989,175 B2
(45) Date of Patent: Jan. 24, 2006

(54) ACYL FLUORIDE ACTIVATION OF CARBOXYSILYL-COATED GLASS SUBSTRATES

(75) Inventor: Raymond C. Milton, La Habra, CA (US)

(73) Assignee: Beckman Coulter, Inc., Fullerton, CA (US)

(*) Notice: Subject to any disclaimer, the term of this patent is extended or adjusted under 35 U.S.C. 154(b) by 712 days.

(21) Appl. No.: 10/094,584

(22) Filed: Mar. 8, 2002

(65) Prior Publication Data

US 2003/0170640 A1    Sep. 11, 2003

(51) Int. Cl.
- B05D 1/36    (2006.01)
- B05D 3/10    (2006.01)
- C07C 17/16   (2006.01)
- C12Q 1/68    (2006.01)

(52) U.S. Cl. .............. 427/333; 427/2.13; 427/301; 427/337; 427/407.2; 435/6; 570/258

(58) Field of Classification Search .............. 427/2.1, 427/2.11, 2.12, 2.13, 299, 301, 331, 333, 427/337, 402, 407.1, 407.2, 444, 445; 435/6; 570/123, 124, 162, 163, 164, 258

See application file for complete search history.

(56) References Cited

U.S. PATENT DOCUMENTS

| | | | |
|---|---|---|---|
| 5,474,796 A | 12/1995 | Brennan | 427/2.13 |
| 5,571,622 A * | 11/1996 | Ogawa et al. | 428/391 |
| 5,843,789 A * | 12/1998 | Nomura et al. | 436/164 |
| 6,013,789 A | 1/2000 | Rampal | 536/25.3 |
| 6,037,124 A | 3/2000 | Matson | 435/6 |
| 6,110,669 A | 8/2000 | Milton | 435/6 |
| 6,146,833 A | 11/2000 | Milton | 435/6 |
| 6,268,141 B1 * | 7/2001 | Matson et al. | 435/6 |
| 2001/0039018 A1 * | 11/2001 | Matson et al. | 435/6 |

FOREIGN PATENT DOCUMENTS

JP    05-192640 A  *  8/1993

OTHER PUBLICATIONS

Blawas, A.S. Protein Patterning. Elsevier Biomaterials 19, 1998 pp. 595-609.
Carpino, Louis A. et al., Peptide Synthesis via Amino Acid Halides. Acc. Chem. Res. 1996, 29, pp. 268-274.
Franz, R. Ueber Trishydrofluoride Tertiaerer Amine Und Ihren Einsatz Als Flourierungsmittel. Journal of Flourine Chemistry, 15 1980 pp. 423-434.
Jedrzejczak, Maria, The kinetics of Aminolysis of Acyl Halides. J. Chem. Soc. Perkin Trans. 2, 1993, pp. 599-600.

* cited by examiner

Primary Examiner—Timothy Meeks
Assistant Examiner—William Phillip Fletcher, III
(74) Attorney, Agent, or Firm—Hogan & Hartson, LLP

(57) ABSTRACT

A method for the acyl fluoride activation of a carboxysilyl-coated glass is described. The method includes providing a glass substrate having a surface with at least one pendant carboxysilyl linker comprising a carboxyl group and activating without etching the surface of the glass by converting the carboxyl group into an acyl fluoride group. In one embodiment, the surface of the glass may be activated by contacting the surface with a fluoridating agent and a tertiary amine reagent, and a solvent that is capable of binding hydrogen fluoride. A substrate for the covalent immobilization of nucleophile-containing species is also provided. The substrate comprises a glass having a surface with a pendant carboxysilyl linker activated by acyl fluoride without etching the surface of the glass. The invention also provides a bioarray formed on a glass surface activated with acyl fluorides without etching.

18 Claims, 4 Drawing Sheets

11500 BAPA IN 50 mM CARBONATE BUFFER pH 9

BIOTINYLATED OLIGONUCLEOTIDE (B-669) IN WATER

BIOTINYLATED OLIGONUCLEOTIDE (B-671) IN WATER 40.9 nM 50% LABELLED c-DNA (ACTIN, ALB5 p.151)

CHES pH 9   CAPS pH 10.5   CARBONATE pH 10

FILE=p041100b                04 11 00
   CHESCAPS                     PJ

ACYL FLUORIDE ACTIVATION OF CARBOXYSILYL-COATED GLASS SUBSTRATES

AREA OF THE ART

The present invention generally relates to methods of preparing glass substrates for the immobilization of molecules, and specifically to carboxysilyl-coated glass substrates activated with acyl fluoride without etching the glass. The invention is also related to bioarrays prepared utilizing such activated glass substrates.

DESCRIPTION OF THE PRIOR ART

Bioassays often require the attachment of biomolecules to solid supports. There are various methods, including adsorption, ultraviolet cross-linking, and covalent attachment, available for such immobilization. Adsorption of biomolecules on surfaces is a relatively simple method driven by ionic, hydrophobic, or Van der Waals attraction forces. However, this method does not provide sufficiently stable immobilization of biomolecules and cells on the substrates. The method also does not afford the precision of biomolecule and cell attachment, which is desired in bioarray construction.

Ultraviolet cross-linking involves the derivatization of a substrate with a photochemical species which, when activated by UV irradiation, can bind target biomolecules. This method, however, is a random process, which does not permit precise array construction. Additionally, the substrates derivatized with photochemical species are sensitive to UV light which leads to difficulties in their storage and use.

A more stable and precise means of biomolecule immobilization is their covalent binding to the surface. However, due to weak interaction between native biomolecules and unmodified substrates, a chemical modification of biomolecules and their substrates is often required in order to promote their efficient binding. For example, U.S. Pat. No. 5,215,882 discloses modifying a nucleic acid with a primary amine, followed by the reaction of the modified nucleic acid with the solid substrate having free aldehyde groups in the presence of a reducing agent. There have been other numerous reports of the immobilization of biomolecules on substrates modified to carry various active groups, including hydroxyl, carboxyl, amine, hydrazine, epoxide, bromoacetyl, maleimide, and thiol (see, for example, a discussion in the Background Section of U.S. Pat. No. 6,013,789 and A. S. Blaws and W. M. Reichert, *Biomaterials* 19: 595–609, 1998).

Other investigators have used bifunctional crosslinkers, such as silanes, for immobilizing biomolecules (U.S. Pat. No. 5,474,796). Recently, an immobilization of unmodified biopolymers to acyl-fluoride-activated substrates has been reported by the assignee of the present invention (U.S. Pat. No. 6,268,141).

Glass is a commonly used solid substrate, because it is inexpensive and because it provides high optical quality. Glass microscope slides, for example, have become the industry standard for microarray work. Various types of pre-derivatized glass substrates are commercially available, including microscope slides coated with poly-L-lysine or amino propyl silane, or glass slides with exposed aldehyde functionalities. However, commercially available glass substrates utilize inferior attachment chemistries, have limited biomolecule binding-selectivity, and have a limited shelf life.

Therefore, it is desirable to develop more effective methods for attaching biomolecules to a glass substrate. It is also desirable to develop convenient, fast, inexpensive, and reliable methods for the activation of glass substrates, particularly glass microscope slides.

SUMMARY OF THE INVENTION

Therefore, it is an object of the present invention to provide a method for the activation of glass substrates which is fully compatible with standard techniques used in genomic and proteomic micro- and macroarray research. It is a further object of the present invention to provide activated glass substrates with reasonable shelf lives, which are stable at ambient conditions, inexpensive, optically clear, and physically rugged. It is another object of the present invention to provide substrates having surfaces suitable for the covalent attachment of molecules, especially biomolecules, such as nucleic acids, proteins and carbohydrates, or their fragmentation products or synthetic replicas.

These and other objects are achieved in the present invention by utilizing acyl fluoride activation chemistry combined with a hydrogen fluoride-neutralizing procedure. The hydrogen fluoride-neutralizing procedure of the present invention advantageously prevents etching of the glass surface during acyl fluoride activation.

Accordingly, one aspect of the present invention provides a method for acyl fluoride activation of a carboxysilyl-coated glass and concomitant neutralization of the hydrogen fluoride side product. The method includes the steps of:
  (a) providing a glass substrate having a surface with at least one pendant carboxysilyl linker comprising a carboxyl group;
  (b) activating the surface of the glass by converting the carboxyl group into an acyl fluoride group; and
  (c) neutralizing a hydrogen fluoride side product of the activating step (b) to prevent etching of the glass.

Those skilled in the art will appreciate that steps (b) and (c) of the method may be carried out simultaneously or consequently as long as hydrogen fluoride is timely neutralized to prevent etching of the glass substrate. In one embodiment, the surface of the glass is activated without etching by contacting the surface with a fluoridating agent in a presence of a tertiary amine reagent and solvent that is capable of neutralizing hydrogen fluoride.

The activation process of the present invention may be applied to commercially available carboxysilyl-coated glass substrates. Alternatively, carboxysilyl glass substrates may be prepared by reacting a glass surface with a carboxysilane reagent under conditions sufficient to form a pendant carboxysilyl linker on the surface. In one embodiment, the carboxysilane reagent is N-[(3-trimethoxysilyl)propyl]ethylene-diamine triacetic acid trisodium salt.

Another aspect of the present invention is directed to a substrate for covalent-immobilizing nucleophile-containing species. The substrate comprises glass having a surface with a pendant carboxysilyl linker that has been activated by acyl fluoride without etching the surface of the glass.

In another aspect, the present invention provides a method of the covalent-immobilization of nucleophile-containing species on a glass substrate. The method includes the steps of:
  (a) providing a nucleophile-containing species;
  (b) providing a glass substrate having a surface with at least one pendant carboxysilyl linker comprising a carboxyl group;
  (c) activating the surface of the glass by converting the carboxyl group into an acyl fluoride group;
  (d) neutralizing a hydrogen fluoride side product of the activating step (c) to prevent etching of the glass surface; and (e) contacting the nucleophile-containing species with the activated glass surface under a condition that allows the covalent binding of the nucleophile-containing species with the acyl fluoride group.

In one embodiment, the nucleophile-containing species is a nitrogen and/or oxygen nucleophile-containing species.

Because the glass substrates of the present invention are activated without etching, they are optically clear and they are well suited for use in the production of macro- and microarrays. Accordingly, a further aspect of the present invention provides bioarrays prepared by a method comprising the steps of:

(a) providing a plurality of biomolecules;
(b) providing a glass having a surface with at least one pendant carboxysilyl linker comprising a carboxyl group;
(c) activating the surface of the glass by converting the carboxyl group into an acyl fluoride group;
(d) neutralizing a hydrogen fluoride side product of the activating step (c) to prevent etching of the glass surface; and
(e) contacting the biomolecules with the activated glass surface at discrete locations under a condition that allows a covalent binding of the biomolecules with the acyl fluoride groups to form a bioarray.

Those skilled in the art will recognize that the activated glass substrates of the present invention may be used for the covalent attachment of any nucleophile-containing material in addition to biomolecules. For example, the activated glass substrates of the present invention may be used for the covalent attachment of histological or other biological materials having amino-, primary or secondary amine-, or hydroxyl-containing functional groups.

Bioarrays prepared on the activated glass substrates of the present invention are compatible with both commercial and homemade microarray printers, as well as confocal laser scanners. The activated glass substrates may be sold to the end-user for bioarray construction. Alternatively, the activated glass substrates of the present invention may be utilized in-house for the production of targeted arrays. Such arrays can be included in kits for use with confocal laser scanners by consumers.

The present invention provides many economic and technical advantages over conventional substrate activation chemistries and conventional glass substrates. Those skilled in the art will appreciate that acyl fluoride groups are relatively resistant to reaction with water, but are highly reactive with nitrogen and/or oxygen nucleophiles ("Peptide Synthesis via Amino Acid Fluorides," Carpino, L., Beyerman, M., Wenschuh, H. & Bienert, M.: *Acc. Chem. Res.:* 29, 268–74, 1996). Because of such low reactivity of acyl fluoride groups toward water, the substrates of the present invention have an extended shelf life, even in humid conditions. Additionally, the tri-substitution of the pendant silyl moieties with acyl fluoride groups further enhances overall reactivity of the activated carboxysilylated glass toward nitrogen and/or oxygen nucleophiles.

The acyl fluoride chemistry is particularly attractive for use in array production because it prevents the problem of "doughnuts." The "doughnut" problem occurs when the printed spots dry on the conventional substrates from the circumference inwards. As a result, the concentration and, hence, the acylation rate at the periphery of the spot increases and a doughnut-shaped binding zone having an uneven distribution of the analyte-binding partner forms. However, when acyl fluoride attachment chemistry is utilized, amino-containing analytes bind to acyl fluoride sites rapidly, before the formation of doughnut-shaped binding zones.

Additionally, because the glass substrate activation of the present invention combines acyl fluoride chemistry with a simultaneous hydrogen fluoride neutralization, the method unexpectedly prevents etching of the surface of the glass during the activation. Such activation without etching produces reactive, yet optically clear, substrates, which are compatible with the standard techniques and equipment used in genomic and proteomic array studies. Finally, the simple two-step activation process of the present invention fully meets the objective of providing a convenient, fast, inexpensive, and reliable glass substrate activation method.

The above-mentioned and other features of this invention and the manner of obtaining them will become more apparent, and will be best understood, by reference to the following description, taken in conjunction with the accompanying drawings. These drawings depict only typical embodiments of the invention and do not limit its scope.

DETAILED DESCRIPTION OF THE INVENTION

Figure 1:
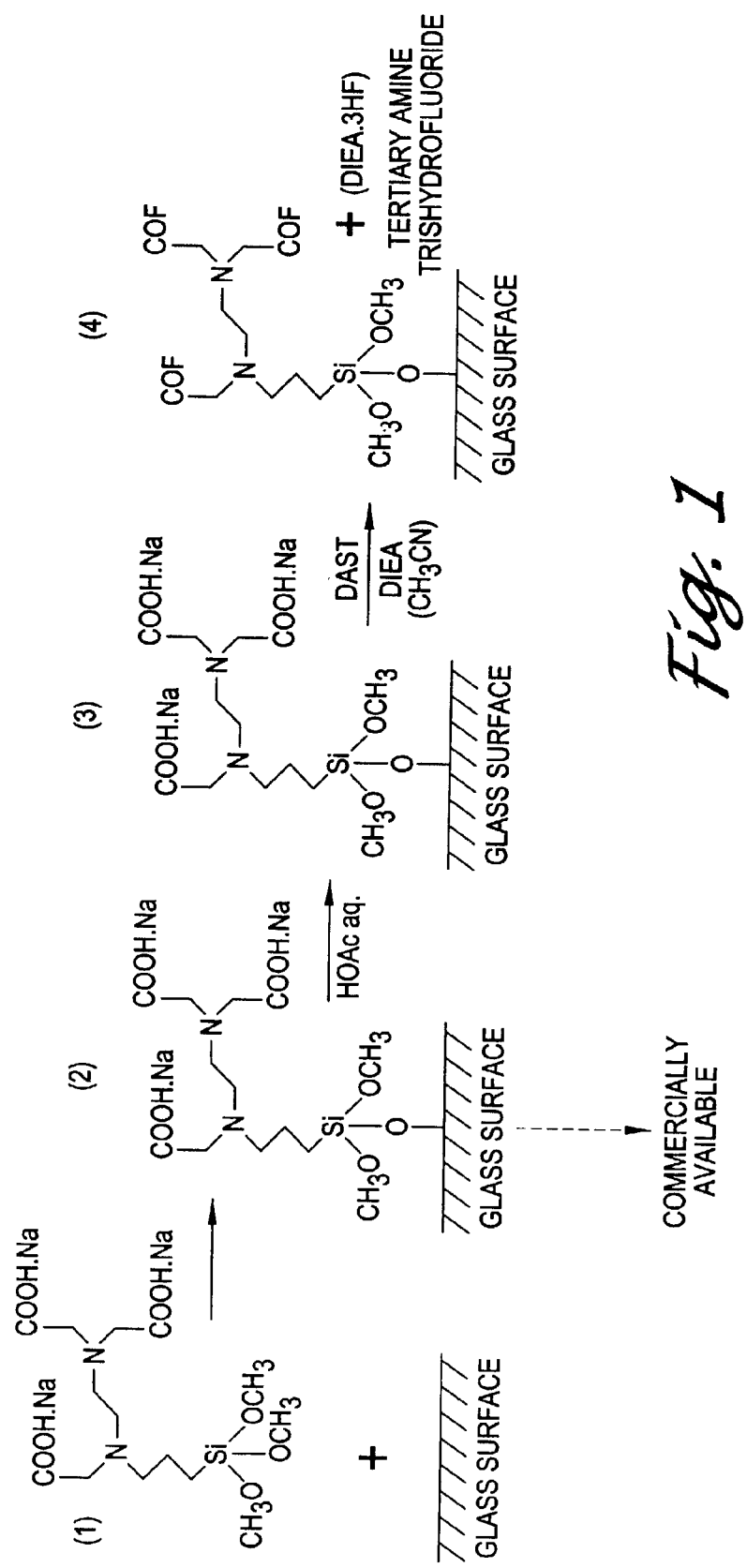
FIG. 1 is a diagram illustrating a method for the acyl fluoride activation of a carboxysilyl-coated glass of the present invention.

An acyl fluoride activation of polymeric supports fabricated from ethylene acrylic acid copolymers, ethylene methacrylic acid copolymers, or derivatized polypropylene has been described in U.S. Pat. Nos. 6,110,669 and 6,146,833, assigned to the assignee of the present invention, the relevant content of which is incorporated herein in its entirety by reference. Such acyl fluoride-activated polymeric substrates have been successfully used to attach amine-modified oligonucleotides (U.S. Pat. Nos. 6,110,669 and 6,146,833), as well as unmodified biopolymers, such as cDNA (U.S. Pat. No. 6,268,141 B1) and protein reagents (co-pending U.S. application Ser. No. 1791-181, entitled "Method for Preparing Multi-Functional Universal Microarrays"). The relevant content of U.S. Pat. No. 6,268,141 B1 and U.S. application Ser. No. 1791-181 is incorporated herein in their entirety by reference.

The successful application of acyl fluoride chemistry to substrate activation for biomolecule attachment can be attributed to unique physical and chemical properties of fluorine. Fluorine has properties distinctively different from other halogens and out of line with the trend in the halogen group of the Periodic Table. For example, while being the most electronegative element, fluorine has electron affinity lower than that of chlorine. The incorporation of fluorine into carbon-containing moieties, such as acyl groups, brings about significant changes in their chemical activity and reaction kinetics.

Due to the singular way the fluorine atom shares electrons in the carbon-fluorine bond, as well as its relative size and ionization energy, acyl fluorides, unlike other acyl halides, are selective towards nitrogen nucleophiles over competing species. The acyl fluorides are less reactive toward neutral oxygen nucleophiles, such as alcohols and almost unreactive with water (Carpino et al., supra at 271), and, therefore, are relatively resistant to hydrolysis. The low reactivity of acyl fluoride with water leads to a great storage stability of acyl-fluoride-activated substrates, even under humid conditions. On the contrary, other acyl halides readily react with trace amounts of water in the air, which hinders the long-term storage of halide-acyl-activated polymeric substrates.

Additionally, the small size of the fluorine atom obviates steric hindrance in the formation of an amide bond. On the contrary, other reactive groups, including some other halogens, often create steric hindrance and, thus, slow down the reaction. The specific reactivity of acyl fluorides for their targets, combined with their stability under aqueous conditions, makes the acyl fluoride activation chemistry highly desirable in applications requiring the covalent attachment of biomolecules to activated supports.

Optically clear glass substrates, such as microscope slides, are often chosen for the preparation of macro- and microbioarrays. The currently used attachment chemistries with glass substrates are inferior to the acyl fluoride chemistry. However, prior to the present invention, acyl fluoride activation has not been applied to glass substrates.

Accordingly, one aspect of the present invention provides a method for the acyl fluoride activation of a carboxysilyl-coated glass. The method includes the steps of:

(a) providing a glass substrate having a surface with at least one pendant carboxysilyl linker comprising a carboxyl group;
(b) activating the surface of the glass by converting the carboxyl group into an acyl fluoride group; and
(c) neutralizing a hydrogen fluoride side product of the activating step (b) to prevent etching of the glass.

The carboxysilyl linker of the present invention is a silane compound containing at least one carboxyl group and having the following general formula:

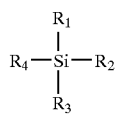

wherein Si is a silicon atom, $R_1$ is a single or branched chain appended by one or more carboxyl groups,and $R_2$, $R_3$, and $R_4$ are independently selected alkoxy or alkyl groups.

In one embodiment, the carboxysilyl linker is N-[(3-trimethoxysilyl)propyl]ethylene-diamine triacetic acid trisodium salt [$(CH_3O)_3$—Si—$(CH_2)_3N(CH_2COOH.Na)$—$(CH_2)_2N(CH_2COOH.Na)_2$]

Acyl fluoride activation involves treating carboxyl groups with a fluoridating agent to convert them into acyl fluoride groups. This reaction, however, leads to the formation of hydrogen fluoride as a side product. Hydrogen fluoride formation is undesirable in the activation of glass substrates because hydrogen fluoride etches glass surfaces, which greatly diminishes their optical properties and makes them unsuitable for use with optical readers. The present invention solves this problem by providing a method of acyl fluoride activation of a carboxysilyl-coated glass surface without the undesirable etching of the glass.

Those skilled in the art will appreciate that the activating and the neutralizing steps of the above method may be carried out simultaneously or consequently as long as hydrogen fluoride is neutralized before it etches the glass substrate. For example, in accordance with one embodiment of the present invention, the surface of the glass is activated by contacting the surface with a fluoridating agent in the presence of a tertiary amine reagent and a solvent that is capable of binding/neutralizing hydrogen fluoride. As a result, the acyl fluoride activation of the glass does not lead to the glass etching.

Suitable reagents for converting carboxyl groups into acyl fluoride groups broadly include carboxyl reactive fluoridating reagents. The most preferred reagent is (diethylaminosulphur) trifluoride (DAST). Other suitable reagents include cyanuric fluoride, tetramethylfluoroformadinium hexafluorophosphate, and tertiary amine trishydrofluorides.

A tertiary amine reagent is added to the reaction mix to prevent etching of the glass surface by the hydrogen fluoride side product. The tertiary amine reagent binds hydrogen fluoride and forms a tertiary amine trishydrofluoride. Tertiary amine trishydrofluoride is known not to corrode borosilicate glass (see the Summary of Ueber Trishydrofluoride Tertiaerer Amine Und Ihren Einsatz Als Fluorierungsmittel, Franz, R.: Journal of Fluorine Chemistry: 15, 423–34, 1980). Additionally, the produced tertiary amine trishydrofluoride is a fluoridating agent in its own right. In a preferred embodiment, the tertiary amine reagent is diisopropylethylamine (DIEA), a sterically hindered tertiary amine.

A solvent is added to the reaction mixture to further neutralize hydrogen fluoride so that it cannot etch the glass surface. Those skilled in the art will appreciate that the solvent may be any solvent capable of neutralizing hydrogen fluoride. In the preferred embodiment, the solvent is acetonitrile because it has a higher affinity to hydrogen fluoride as compared to other halogen acids (paragraph one, page 430: Ueber Trishydrofluoride Tertiaerer Amine Und Ihren Einsatz Als Fluorierungsmittel, Franz, R.: Journal of Fluorine Chemistry: 15, 423–34, 1980).

The acyl fluoride activation of carboxysilyl glass substrates can be carried out under any conditions that allow the conversion of carboxyl groups into acyl fluoride groups without etching the glass surface. In one embodiment, after removal of the sodium salt, the carboxysilyl-coated glass substrates are activated by immersion in a solution of an excess of DAST and DIEA in dry acetonitrile (stored over 3 Å sieve) for 25 minutes (5% v/v for DAST and 2.5% v/v DIEA). Then, the slides are washed by immersion three times in dry acetonitrile (stored over 3 Å sieve) and were dried.

Carboxysilyl glass slides can be purchased from CEL Associates, Inc. (Houston, Tex.). Alternatively, the carboxysilyl-coated glass may be prepared by:

(a) providing a glass having a surface; and
(b) reacting the surface of the glass with a carboxysilyl reagent under conditions sufficient to form the carboxysilyl linker on the surface.

Those skilled in the art will realize that the present method is suitable for coating any type of glass. For example, glass chemistry (major, minor, and trace metal composition) and its physical properties are not crucial for the application of the present invention.

Any carboxysilyl agent may be used as long as it is capable of covalent attachment to the glass surface. For example, in one embodiment, the carboxysilylreagent is N-[(3-trimethoxysilyl)propyl]ethylene-diamine triacetic acid trisodium salt.

The conditions of a reaction between the surface of the glass and a carboxysilyl agent are sufficient if the conditions allow the formation of the pendant carboxysilyl linker on the glass surface. For example, in one embodiment, a glass substrate is immersed in an aqueous solution of N-[(3-trimethoxysilyl)propyl]ethylene-diamine triacetic acid trisodium salt at room temperature and centrifuged to dry prior to curing.

In one embodiment, the carboxysilyl reagent is in a salt conjugate form. When such a reagent reacts with the glass surface, pendant acyl fluoride linkers formed on the surface of the glass may also be in a salt conjugate form and have to be neutralized to expose carboxyl groups for their further conversion into acyl fluoride groups (FIG. 1). In one embodiment, the carboxysilyl reagent in a salt conjugate form is N-[(3-trimethoxysilyl)propyl]ethylenediamine triacetic acid trisodium salt. The sodium salt may be neutralized with excess acetic acid in an aqueous solution (10% v/v for 10 minutes) as explained in detail in Example 1 of the present disclosure.

Substrate-linked acyl fluorides are reactive with nucleophiles. In particular, although substrate-linked acyl fluorides are relatively unreactive with water, they readily and selectively react with amino-, primary or secondary amine-, and hydroxyl-containing nucleophiles species with a formation of a covalent bond. Substrate-linked acyl fluorides may also react with some ester-containing species to link them to the substrate. Therefore, acyl fluoride-activated glass slides may be used for the covalent immobilization of a broad range of organic molecules and biomolecules containing nucleophile groups, in particular nitrogen and/or oxygen nucleophiles.

Accordingly, in another aspect, the present invention provides a substrate for the covalent immobilization of nucleophile-containing species. The substrate comprises a glass surface with a pendant carboxysilyl linker activated by a reaction with a fluoridating agent without etching the surface of the glass. In a preferred embodiment, nitrogen and/or oxygen nucleophile-containing species are immobilized on the glass substrates of the present invention.

The substrate of the present invention may be in any form as long as it provides a surface or surfaces available for the attachment of molecular species. Examples of suitable forms of the substrate include, but are not limited to, slides, sheets, and beads. The substrate of the present invention is particularly useful in the preparation of biomolecular arrays for the evaluation or identification of biological activity. Accordingly, in one embodiment, the solid support is in the form of a device having at least one flat planar surface. The size of the solid support can vary and depends upon the final use of the immobilized biomolecules. Those skilled in the art will appreciate that, for example, arrays of biopolymers immobilized on miniaturized solid supports have been under development for many years. These solid supports have a size area on the order of $mm^2$ and can have numerous different immobilized biopolymers attached to different site-specific locations on the miniaturized solid support.

The term "biomolecule," as used herein, refers to nucleic acids, polynucleotides, polypeptides, proteins, carbohydrates, lipids, other biologically significant species, and analogues thereof. As used herein, "polynucleotide" refers to a polymer of deoxyribonucleotides or ribonucleotides in the form of a separate fragment or as a component of a larger construction. "Polynucleotide," as used herein, may be DNA, RNA, a DNA analog such as PNA (peptide nucleic acid), or a synthesized oligonucleotide. The DNA may be a single- or double-strand DNA, or a DNA amplified by PCR technique. The RNA may be an mRNA. The length of the polynucleotides may be 3 bp to 10 kb. In accordance with one embodiment of the present invention, the length of a polynucleotide is in the range of about 50 bp to 10 kb, preferably, 100 bp to 1.5 kb. In accordance with another embodiment of the present invention, the length of a synthesized oligonucleotide is in the range of about 3 to 100 nucleotides.

As used herein, the term "polypeptide" refers to a polymer of amino acids, wherein the α-carboxyl group of one amino acid is joined to the α-amino group of another amino acid by a peptide bond. A protein may comprise one or multiple polypeptides linked together by disulfide bonds or other noncovalent interactions. Examples of the protein include, but are not limited to, antibodies, antigens, enzymes, and receptors.

The substrate of the present invention is well suited for the covalent attachment of a nucleophile-containing species. Accordingly, in a further aspect, the present invention provides a method for the covalent attachment of a nucleophile-containing species to a glass substrate. The method comprises the steps of:
 (a) providing a nucleophile-containing species;
 (b) providing a glass substrate having a surface with at least one pendant carboxysilyl linker comprising a carboxyl group;
 (c) activating the surface of the glass by converting the carboxyl group into an acyl fluoride group;
 (d) neutralizing a hydrogen fluoride side product of the activating step (c) to prevent etching of the glass surface; and
 (e) contacting the nucleophile-containing species with the activated glass surface under a condition that allows covalent binding of the nucleophile-containing species with the acyl fluoride group.

The nucleophile-containing species are covalently attached to the activated glass substrate of the present invention by contacting them under a condition sufficient for allowing the attachment of these species to the glass substrate. A condition is sufficient if it allows the molecules to react with the pendant acyl fluoride groups of the linker to form a covalent bond.

In accordance with one embodiment of the present invention, the step of contacting the polynucleotides with the coated substrate is accomplished in the presence of an aqueous buffer, preferably with a neutral or basic pH. For the purpose of the present invention, a basic pH condition is a condition that has a pH greater than 8. A basic pH condition is sufficient if it allows the attachment of the polynucleotides to the solid support. In accordance with one embodiment of the present invention, the basic pH condition of the present invention has a pH of about 9 to 12. It should be understood that the basic pH condition may vary, depending on the method used. One skilled in the art can readily ascertain the basic pH condition of a particular attachment reaction in view of the disclosure of the present invention.

Examples of suitable conditions for the covalent attachment of different types of molecules are provided below (Examples 2–4). In summary, in one embodiment, an activated glass slide is hand-spotted with an aqueous solution of biotinylated oligonucleotide (~20 nM at neutral pH) and dried at room temperature. In another embodiment, a 0.02 mg/ml solution of rabbit-α-mouse IgG in three different buffers is printed on three activated slides with a BioDot ink jet printer and dried at room temperature. The buffers are 50 mM CHES pH 9.0, 50 mM CAPS pH 10.5, and 0.1M carbonate pH 10.0. In still another embodiment, a 1:500 dilution of biotinamidepentylamine (BAPA) in 50 mM carbonate buffer pH 10 is printed on two activated slides with a Biodot ink jet printer.

An activated glass substrate of the present invention may be contacted with the nucleophile-containing species by methods that are known in the art. For example, the contacting step may be carried out by ink jet printing, solid or open capillary device contact printing, microfluidic channel printing, and a technique using printing devices based upon electrochemical or electromagnetic forces. For example, thermal inkjet printing techniques utilizing commercially available ink jet printers and piezoelectric microjet printing techniques, as described in U.S. Pat. No. 4,877,745, can be utilized to spot unmodified polynucleotides to solid supports. Alternatively, the contacting step may be carried out by manually spotting the biomolecules or cells on the activated glass substrate with a pipettor or with a Biomek pin tool.

It should be understood that the coated substrates of the present invention may be contacted with the nucleophile-containing species, including biomolecules, by any methods as long as the molecules are put in contact with the glass substrate. It should also be understood that other aqueous buffer systems, which are not explicitly described here, may also be used in the present invention as long as the buffer system provides a sufficient condition that allows the attachment of molecules to the glass substrate.

In accordance with embodiments of the present invention, the concentration of molecules contained in aqueous solutions may vary, depending on the types of the molecules, their size, structure, and other factors that may influence the solubility of the molecules. Generally, a molar excess of nucleophilic species being printed over the acyl fluoride groups on the surface of the substrate is required. For example, when the attached polymers are polynucleotides, preferably, their concentration in the solution being printed is in the range from about 5 nM to about 40 $\mu$M.

In one embodiment, the unreacted pendant acyl fluoride groups are "blocked" from further unwanted reactions. The pendant acyl fluoride groups may be blocked by any chemicals that can inactivate them. For example, unreacted acyl fluoride functionalities may be reacted with ammonium hydroxide to form carboxamide or with ethanol to form esters. Those skilled in the art will recognize, however, that a host of other blocking reactions are possible.

As mentioned above, many applications for utilizing immobilized biomolecules require that the biomolecules are immobilized at site-specific locations on a solid support surface. In order to prepare ordered arrays of biomolecules, including grids and arrays of immobilized biomolecules with each biomolecule located at site-specific locations, a preselected site on the surface of the coated substrate is exposed to a solution of the desired biomolecules or cells. This can be accomplished manually or by utilizing various printing techniques discussed above.

Consequently, another aspect of the present invention provides a bioarray prepared by a method comprising the steps of:

(a) providing a plurality of biomolecules;
(b) providing a glass substrate having a surface with at least one pendant carboxysilyl linker comprising a carboxyl group;
(c) activating the surface of the glass by converting the carboxyl group into an acyl fluoride group;
(d) neutralizing a hydrogen fluoride side product of the activating step (c) to prevent etching of the glass surface; and
(e) contacting the biomolecules with the activated glass surface at discrete locations under a condition that allows a covalent binding of the biomolecules with acyl fluoride groups to form a bioarray.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLES

Example 1

Activating Carboxysilyl Glass:

Carboxysilyl glass slides were prepared by immersing borosilicate glass microscope slides in a 2% aqueous solution of the N-[(3-trimethoxysilyl)propyl]-ethylenediamine triacetic acid trisodium salt reagent (United Chemical Technologies, Inc., Bristol, Pa.) with agitation at room temperature for two to three minutes prior to drying and curing at room temperature for 24 hours. Alternatively, pre-made carboxysilyl glass slides may be purchased from CEL Associates, Inc. (Houston, Tex.) or another supplier. Residualsodium salt was neutralized with excess acetic acid in aqueous solution (10% v/v for 10 minutes) to free the carboxyl groups and washed by immersion three times in water. The slides were dried under a strong stream of argon gas (~90 psi), although low speed centrifugation may be used more effectively. The dried, neutralized slides were subsequently activated by immersion in a solution of an excess of DAST and DIEA in dry acetonitrile (stored over 3 Å sieve) for 25 minutes (5% v/v for DAST and 2.5% v/v DIEA).

The slides were washed by immersion three times in dry acetonitrile (stored over 3 Å sieve) and were dried under a strong stream of argon gas (~90 psi), although low speed centrifugation may have been used more effectively. The activated slides were stored under argon at 4° C. or lower.

Example 2

Covalent Attachment of Oligonucleotides and cDNA to the Activated Slides of the Present Invention.

An activated glass slide prepared in accordance with Example 1 was hand-spotted with solutions of biotinamidopentylamine (BAPA) in a basic carbonate buffer (pH 9), two biotinylated oligonucleotides in water (neutral pH), and a cDNA preparation also in water (neutral pH). After drying at room temperature for less than five minutes, the remaining activated sites on the slide were quenched with ethanol for an hour. The ethanol used probably was not completely dry as was judged by the "comet tailing" of the spots. The slide was developed with streptavidin-alkaline phosphatase for one hour at ambient temperature. The slide was then placed in enzyme-linked fluorescence (ELF) reagent (fluorescent substrate for alkaline phosphatase, Molecular Probes, Inc., Eugene, Oreg.) for signal development for 30 minutes. The array signal was read using a CCD camera system.

Figure 2:
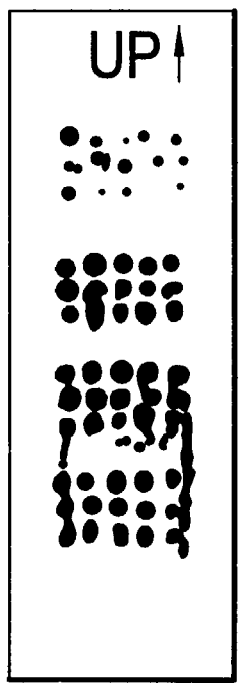
FIG. 2 shows the attachment of oligonucleotides and cDNA to the activated slides of the present invention.

The results, shown in FIG. 2, demonstrate that oligonucleotides and nucleic acids that are attached in an array via the acyl fluoride chemistry to unetched glass surfaces are able to interact biochemically with reporter molecules to produce a detectable signal. A smaller organic molecule (biotinamidopentylamine—BAPA) was also bound, but gave a less intense signal on reaction with streptavidin-alkaline phosphatase and ELF reagent (Molecular Probes, Inc., Eugene, Oreg.)

Example 3

Covalent Attachment of an Antibody to the Activated Glass Slides of the Present Invention.

A 0.02 mg/ml solution of rabbit-α-mouse IgG in three different buffers was printed on three activated slides with a BioDot ink jet printer. The buffers were 50 mM CHES (pH 9.0), 50 mM CAPS (pH 10.5), and 0.1 M carbonate (pH 10.0). After drying, the remaining activated sites on the slide were quenched in a solution of 1 mg/ml casein in 50 mM carbonate (pH 9). A target biotinylated mouse-α-human IgG was then bound to the immobilized α-mouse IgG. The slide was developed with streptavidin-alkaline phosphatase for one hour at ambient temperature. The slide was then placed into the ELF reagent (Molecular Probes, Inc.) for signal development for 30 minutes. The array signal was read using a CCD camera system.

Figure 3:
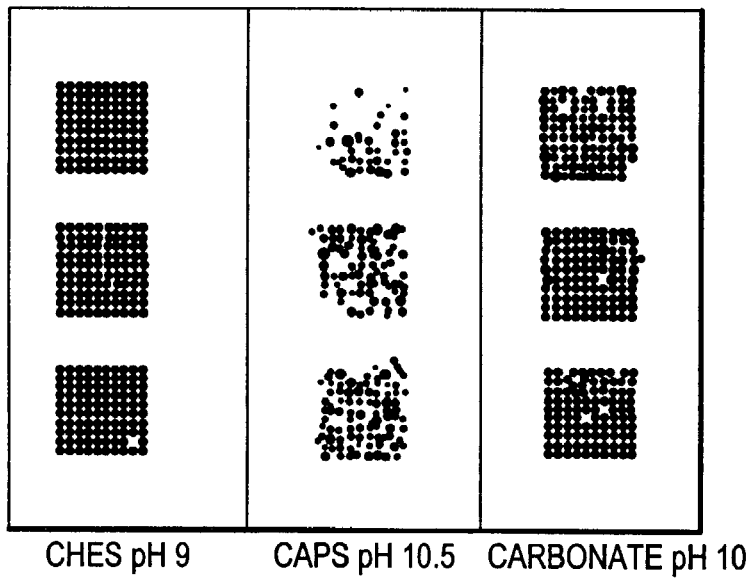
FIG. 3 demonstrates the attachment of an antibody to the activated slides of the present invention.

The results, shown in FIG. 3, demonstrate the attachment of a complex quaternary IgG protein, to the unetched glass surface via the acyl fluoride chemistry using a variety of buffers. The attached protein could be subsequently bound by another biotinylated specific antibody in an immune reaction and detected by a biochemical reporter system consisting of strepavidin-alkaline phosphatase and ELF reagent (Molecular Probes, Inc.).

Example 4

Covalent Attachment of Biotinamidopentylamine (BAPA) to the Activated Glass Slides of the Present Invention.

Biotinamidopentylamine (BAPA) is a small molecular species with a single amino group and, hence, it is easily displaced from a substrate by a competing base unless it is covalently linked to the substrate. A 1:500 dilution of BAPA in 50 mM carbonate buffer pH 10.0 was printed on two activated slides with a Biodot ink jet printer. One slide was incubated in a strongly basic 30% aqueous ammonia solution for 90 minutes, while the other was incubated in ethanol for 90 minutes. Both incubations were carried out at ambient temperature. The slides were developed with streptavidin-alkaline phosphatase for one hour at ambient temperature. The slides were then placed into an ELF reagent for signal development for 30 minutes. The array signal was read using a CCD camera system.

Figure 4:
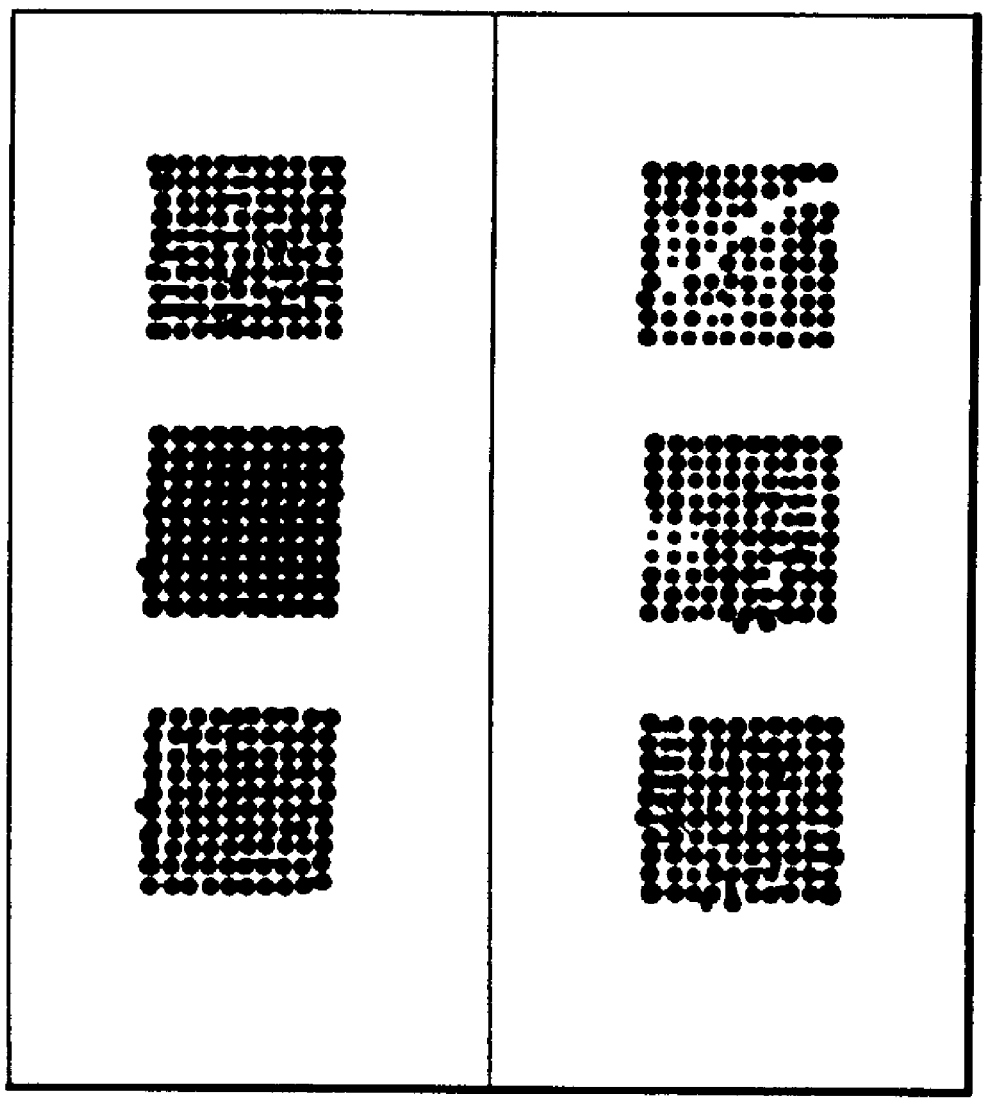
FIG. 4 shows the covalent attachment of biotinamidopentylamine (BAPA) to the activated slides of the present invention.
Figure 5:
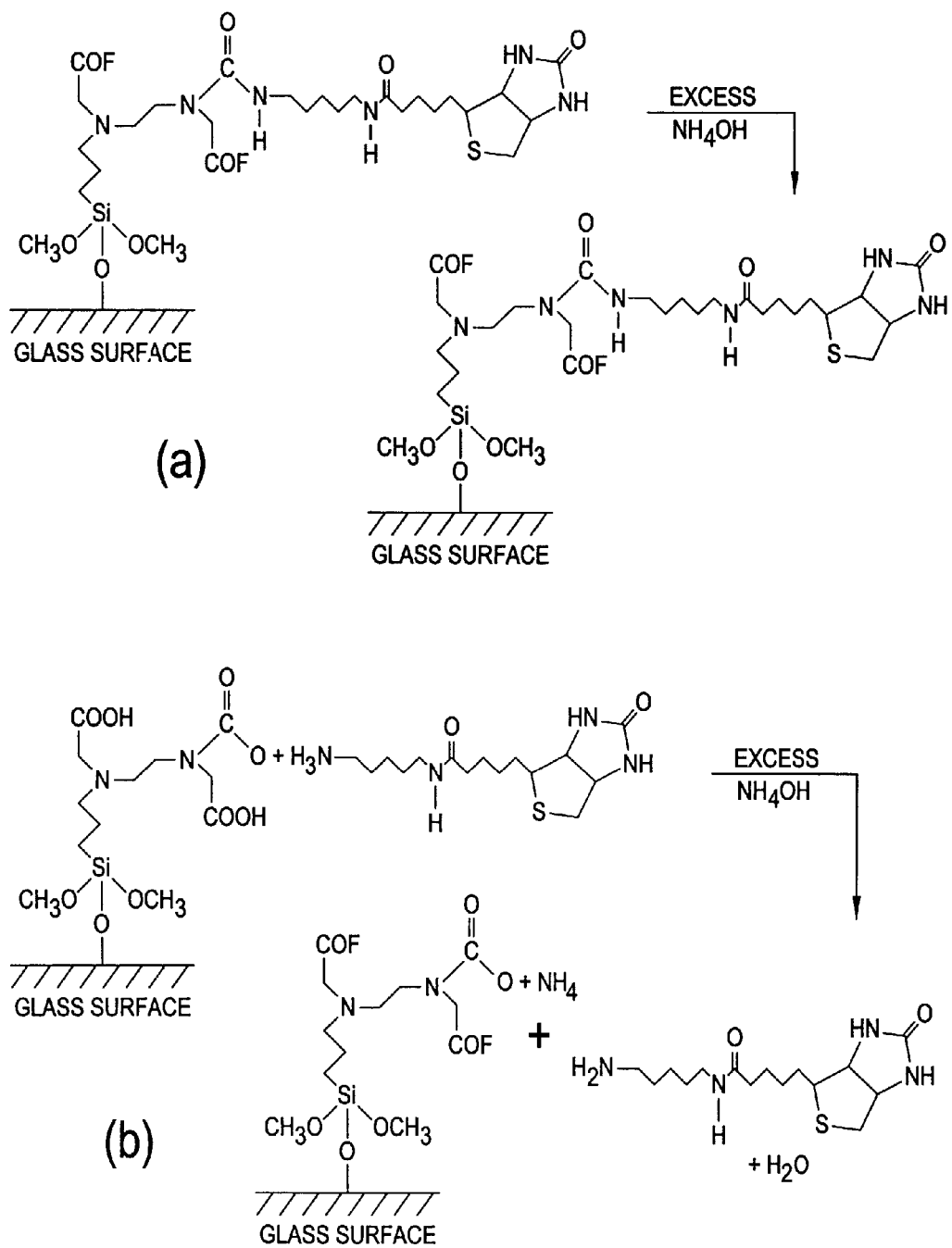
FIG. 5 is a diagram illustrating that BAPA is displaced by competing aqueous ammonia (b), unless BAPA is covalently attached to the activated glass of the present invention (a).

Both reagents, ammonia and ethanol, are expected to quench the unreacted acyl fluoride sites on the slide. Additionally, the ammonia solution is capable of competing off the BAPA if it is not linked to the surface by a covalent amide bond, as schematically shown in FIG. 5b. Since BAPA was not replaced by ammonia, it is concluded that BAPA binds covalently to the silyl linker (FIG. 4), thus, validating the acyl fluoride attachment mechanism.

While the foregoing has been described in considerable detail and in terms of preferred embodiments, these are not to be construed as limitations on the disclosure or claims to follow. Modifications and changes that are within the purview of those skilled in the art are intended to fall within the scope of the following claims.

What is claimed is:

1. A method for acyl fluoride activation of a carboxysilyl-coated glass, comprising the steps of:
   (a) providing a glass substrate having a surface with at least one pendant carboxysilyl linker comprising a carboxyl group;
   (b) activating the surface of the glass substrate by converting the carboxyl group into an acyl fluoride group; and
   (c) neutralizing a hydrogen fluoride side product of the activating step (b) to prevent etching of the glass surface.

2. The method of claim 1, wherein step (a) further comprises the steps of:
   (d) providing a glass substrate having a surface with at least one pendant carboxysilyl linker comprising a pendant carboxyl group in a salt conjugate form; and
   (e) neutralizing the conjugate to expose the carboxyl group.

3. The method of claim 2, further comprising the steps of:
   (f) providing a glass substrate having a surface; and
   (g) reacting the surface of the glass substrate with a carboxysilyl reagent under conditions sufficient to form the pendant carboxysilyl linker on the surface, wherein steps (f) and (g) are carried out before the step (d).

4. The method of claim 3, wherein the carboxysilyl reagent is a silane appended by one or more carboxyl groups.

5. The method of claim 4, wherein the carboxysilyl reagent is N-[(3-trimethoxysilyl)propyl]ethylene-diamine triacetic acid trisodium salt and wherein the formed triacetic acid trisodium salt conjugate is neutralized with excess acetic acid in aqueous solution.

6. The method of claim 1, wherein steps (b) and (c) are carried simultaneously and the surface of the glass is activated by contacting the surface with a fluoridating agent, a tertiary amine reagent, and a solvent that is capable of binding hydrogen fluoride.

7. The method of claim 6, wherein the fluoridating agent is selected from the group consisting of (diethylamino)sulfur trifluoride (DAST), cyanuric fluoride, tetramethylfluoroformadinium hexafluorophosphate, and tertiary amine trishydrofluorides.

8. The method of claim 6, wherein the amine agent is an organic tertiary amine reagent selected from a group consisting triethylamine, trimethylamine, dimethylamine, dimethylbutylamine, and diisopropylethylamine (DIEA).

9. The method of claim 6, wherein the solvent is selected from the group consisting of solvents capable of neutralizing hydrogen.

10. The method of claim 6, wherein the fluoridating agent is DAST, the tertiary amine reagent is DIEA, and the solvent is acetonitrile.

11. A method of covalently immobilizing nucleophile-containing species on glass, comprising:
    (a) providing a nucleophile-containing species;
    (b) providing a glass substrate having a surface with at least one pendant carboxysilyl linker comprising a carboxyl group;
    (c) activating the surface of the glass by converting the carboxyl group into an acyl fluoride group;
    (d) neutralizing a hydrogen fluoride side product of the activating step (c) to prevent etching of the glass surface; and
    (e) contacting the nucleophile-containing species with the activated glass surface under a condition that allows covalent binding of the nucleophile-containing species with the acyl fluoride group.

12. The method of claim 11, wherein the steps (c) and (d) are carried out simultaneously and the surface of the glass is activated by contacting the surface with a fluoridating agent and a tertiary amine reagent and a solvent that is capable of binding hydrogen fluoride.

13. The method of claim 12, wherein the tertiary amine reagent is DIEA.

14. The method of claim 12, wherein the solvent is selected from the group consisting of solvents capable of neutralizing hydrogen fluoride.

15. The method of claim 12, wherein the fluoridating agent is DAST, the tertiary amine reagent is DIEA, and the solvent is acetonitrile.

16. The method of claim 15, wherein the nucleophile-containing species are selected from a group consisting of amino-, primary or secondary amine-, and hydroxyl-containing species.

17. The method of claim 15, wherein the nucleophile-containing species are biomolecules selected from a group consisting of nucleic acids, polynucleotides, polypeptides, proteins, carbohydrates, lipids, and analogs thereof.

18. The method of claim 17, wherein a plurality of biomolecules is provided and wherein the contacting step comprises contacting the biomolecules with the activated glass surface at discrete locations, whereby a bioarray is formed.

* * * * *